United States Patent
Manzer et al.

(10) Patent No.: US 6,602,921 B2
(45) Date of Patent: Aug. 5, 2003

(54) PROCESS FOR THE PREPARATION OF HYDROCARBONS

(75) Inventors: Leo E. Manzer, Wilmington, DE (US); Stephan Schwarz, Wilmington, DE (US); Sergej Maslov, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 09/850,957

(22) Filed: May 8, 2001

(65) Prior Publication Data

US 2002/0028853 A1 Mar. 7, 2002

Related U.S. Application Data

(60) Provisional application No. 60/202,611, filed on May 9, 2000.

(51) Int. Cl.⁷ ............................................... C07C 27/00
(52) U.S. Cl. .................. 518/715; 518/709; 518/717; 518/721
(58) Field of Search ................. 518/715, 717, 518/721, 709

(56) References Cited

U.S. PATENT DOCUMENTS 2,363,739 A   11/1944  Meisenheimer et al. . 260/449.6
4,663,355 A * 5/1987  Coughlin ...................... 518/713
6,313,062 B1 * 11/2001 Krylova et al. ............. 502/326

FOREIGN PATENT DOCUMENTS

WO    WO86/00295    1/1986    ............. C07C/1/04

OTHER PUBLICATIONS

Schanke et al, Study of Pt–promoted cobalt carbon monoxide hydrogenation catalyst, Journal of Catalysis 156 (1) 85–95 (1995).*
PCT Search Report for PCT/US01/14738 dated Oct. 16, 2001.

* cited by examiner

Primary Examiner—J. Parsa
(74) Attorney, Agent, or Firm—Conley Rose, P.C.

(57) ABSTRACT

A Fischer-Tropsch process for producing hydrocarbons, comprising contacting a feed stream comprising hydrogen and carbon monoxide with a catalyst in a reaction zone maintained at conversion-promoting conditions effective to produce an effluent stream comprising hydrocarbons, wherein the catalyst comprises at least one catalytically active metal selected from the group consisting of cobalt, iron, nickel and ruthenium and combinations thereof, a catalyst support, and silver. The catalyst may include a promoter. A preferred catalyst comprises cobalt, platinum and/or ruthenium and/or rhenium, and silver supported on a support selected from the group consisting of $Al_2O_3$, $ZrO_2$, sulfated $ZrO_2$, $WO_3$—$ZrO_2$, MCM-41, H-Beta, Sylopol $SiO_2$, $AlF_3$, fluorided $Al_2O_3$, bentonite, zeolite, $TiO_2$, and $SiO_2$—$Al_2O_3$, molecular sieves, and combinations thereof.

13 Claims, No Drawings

PROCESS FOR THE PREPARATION OF HYDROCARBONS

CROSS-REFERENCE TO RELATED APPLICATIONS

This application claims the benefit under 35 U.S.C. § 119(e) of U.S. Provisional Patent Application No. 60/202,611 filed May 9, 2000.

STATEMENT REGARDING FEDERALLY SPONSORED RESEARCH OR DEVELOPMENT

Not Applicable.

The present invention relates to a process for the preparation of hydrocarbons from synthesis gas, i.e., a mixture of carbon monoxide and hydrogen, typically labeled the Fischer-Tropsch process. More particularly, this invention relates to the use of silver-modified catalysts for the Fischer-Tropsch process. Still more particularly, the present invention relates to a method for improving the yield of desirable high-carbon-number reaction products by using certain silver-containing catalysts.

BACKGROUND

Large quantities of methane, the main component of natural gas, are available in many areas of the world, and natural gas is predicted to outlast oil reserves by a significant margin. However, most natural gas is situated in areas that are geographically remote from population and industrial centers. The costs of compression, transportation, and storage make its use economically unattractive. To improve the economics of natural gas use, much research has focused on the use of methane as a starting material for the production of higher hydrocarbons and hydrocarbon liquids, which are more easily transported and thus more economical. The conversion of methane to hydrocarbons is typically carried out in two steps. In the first step, methane is converted into a mixture of carbon monoxide and hydrogen (i.e., synthesis gas or syngas). In a second step, the syngas is converted into hydrocarbons.

This second step, the preparation of hydrocarbons from synthesis gas, is well known in the art and is usually referred to as Fischer-Tropsch synthesis, the Fischer-Tropsch process, or Fischer-Tropsch reaction(s). Fischer-Tropsch synthesis generally entails contacting a stream of synthesis gas with a catalyst under temperature and pressure conditions that allow the synthesis gas to react and form hydrocarbons.

More specifically, the Fischer-Tropsch reaction is the catalytic hydrogenation of carbon monoxide to produce any of a variety of products ranging from methane to higher alkanes and aliphatic alcohols. The methanation reaction was first described in the early 1900's, and the later work by Fischer and Tropsch dealing with higher hydrocarbon synthesis was described in the 1920's. The first major commercial use of the Fischer-Tropsch process was in Germany during the 1930's. More than 10,000 B/D (barrels per day) of products were manufactured with a cobalt based catalyst in a fixed-bed reactor. Fischer and Pichler described this work in German Patent 731,295, issued Aug. 2, 1936. Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research continues on the development of more efficient Fischer-Tropsch catalyst systems and reaction systems that increase the selectivity for high-value hydrocarbons in the Fischer-Tropsch product stream. In particular, there remains a need for catalysts that produce various desired reaction products. The products of the Fischer-Tropsch hydrogenation reaction can range from molecules containing a single carbon to those containing ten, fifteen or more carbons. Single-carbon hydrocarbon molecules are methane, which is the original gas that was converted into synthesis gas in the first step of the two-step process. The multi-carbon products include gasoline, diesel fuel, jet fuel, and various other relatively valuable hydrocarbons that are, notably, liquids at room temperature.

There are continuing efforts to find catalysts that are more effective at producing these desired products. Product distribution, product selectivity, and reactor productivity depend heavily on the type and structure of the catalyst and on the reactor type and operating conditions. It is highly desirable to maximize the production of high-value liquid hydrocarbons, such as hydrocarbons with five or more carbon atoms per hydrocarbon chain.

U.S. Pat. No. 4,619,910 issued on Oct. 28, 1986, and U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. The catalysts are activated in a fixed-bed reactor by reaction with $CO+H_2$ prior to slurrying in the oil phase in the absence of air. U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania as a hydrocarbon synthesis catalyst. U.S. Pat. No. 4,088,671 discloses a cobalt-ruthenium catalyst where the support can be titania but is preferably alumina for economic reasons. U.S. Pat. No. 4,413,064 discloses an alumina-supported catalyst having cobalt, ruthenium and a Group 3 or Group 4 metal oxide, e.g., thoria. European Patent 142,887 discloses a silica supported cobalt catalyst together with zirconium, titanium, ruthenium and/or chromium.

Despite the vast amount of research effort in this field, Fischer-Tropsch catalysts that can be used to more efficiently produce the desired hydrocarbon products are desired. There is still a great need to identify effective catalysts for Fischer-Tropsch synthesis; particularly catalysts that provide high $C_{11+}$ hydrocarbon production, so as to maximize the value of the hydrocarbons produced and thus maximize the process economics. For successful operation on a commercial scale, the Fischer-Tropsch process must be able to achieve a high conversion of the methane feedstock at high gas hourly space velocities, while maintaining high selectivity of the process to the desired products of carbon monoxide and hydrogen. Accordingly, it is desired to provide catalysts that are selective for specified products and also produce useful amounts of the desired products.

Productivity, which is defined as grams of desired product/kg catalyst/hour, is, of course, the lifeblood of a commercial operation. High productivities are essential in achieving commercially viable operations. Accordingly, an important and necessary objective in the production and development of catalysts is to produce catalysts that are capable of high productivity.

U.S. Pat. No. 4,663,355 discloses the addition of gold, silver or copper to a Fischer-Tropsch catalyst comprising cobalt. The '355 patent purports to show that the addition of gold to the cobalt catalyst reduces the catalyst selectivity for methane in the Fischer-Tropsch reaction. Nevertheless, there is still a need for improvement; particularly, a catalyst is needed that has higher $C_{11}$ production.

SUMMARY OF THE INVENTION

This invention provides a process and system for producing $C_{5+}$ hydrocarbons, and preferably $C_{11+}$. A preferred embodiment of the process comprises; contacting a feed stream comprising hydrogen and carbon monoxide with a catalyst in a reaction zone maintained at conversion-promoting conditions effective to produce an effluent stream. A preferred catalyst comprises (a) at least one metal selected from the group consisting of cobalt and ruthenium, (b) a catalyst support comprising alumina, zirconia, silica, aluminum fluoride, fluorided alumina, bentonite, titania, silica-alumina, sulfated zirconia, tungsten doped zirconia, or molecular sieves, and (c) silver. According to a preferred embodiment, the silver is present in an amount of from about 0.01% to about 10% based on the total weight of the catalyst.

DETAILED DESCRIPTION

It has been discovered that the addition of silver to a cobalt-containing Fischer-Tropsch catalyst significantly improves the $C_{11+}$ productivity of the catalyst, as compared to the same catalyst in the absence of silver. Likewise, the addition of silver to a cobalt-containing catalyst causes an increase in the olefin/paraffin ratio of the produced hydrocarbons. In particular, it has been found that, for some catalysts, the $C_{11+}$ productivity is increased by as much as twenty percent.

Catalyst

According to a preferred embodiment of the invention, silver is added in an amount ranging from about 0.01% to about 10% based on the total weight of the catalyst and support. The catalysts of the present invention comprise silver in combination with a cobalt-containing catalyst on a suitable support. Suitable supports are described in detail below. Alternatively, the cobalt catalyst may be used without a support. In this case, the catalyst may be prepared in the form of cobalt oxide. Catalytically active metal components or promoters may be present in addition to the cobalt, if desired. Examples of suitable Fischer Tropsch promoters include Na, K, Rb, Cs, Mg, Ca, Sr, Ba, Cu, Ag, Au, Sc, Y, La, Ti, Zr, Hf, V, Nb, Ta, Rh, Pd, Os, Ir, Pt, Mn, B, P, and Re.

The present catalyst preferably contains from 2 to 35% by weight, especially from 5 to 25% by weight, of cobalt, but catalysts wherein the catalytic metal is selected from iron, cobalt, nickel and/or ruthenium are all contemplated. Normally, the catalytic metal is reduced to provide elemental metal (e.g., elemental iron, cobalt, nickel and/or ruthenium) before use. The catalyst must contain a catalytically effective amount of the metal component(s). The amount of catalytic metal present in the catalyst may vary widely. Typically, the catalyst comprises from about 1 to 50% by weight (as the metal) of total supported iron, cobalt, nickel, platinum, rhodium, rhenium, and/or ruthenium per total weight of catalytic metal and support, preferably from about 1 to 30% by weight. Each of the metals can be used individually or in combination, especially cobalt and ruthenium. Of particular note are catalysts comprising from about 10 to 25% by weight (e.g., about 20% by weight) of a combination of cobalt and ruthenium where the ruthenium content is from about 0.001 to about 1 weight %.

In addition, the present catalyst may include one or more additional promoters or modifiers known to those skilled in the art. When the catalytic metal is cobalt, and/or ruthenium, suitable promoters include at least one metal selected from the group consisting platinum and rhenium. The amount of additional promoter, if present, is typically between 0.001 and 1 parts by weight per 100 parts of carrier.

Catalyst Support

Support materials that are suitable for use with the present invention include, but are not limited to alumina, zirconia, silica, aluminum fluoride, fluorided alumina, bentonite, titania, ceria, zinc oxide, silica-alumina, and molecular sieves. The support may itself have some catalytic activity. By aluminum fluoride is meant at least one of aluminum fluoride (e.g., alpha $AlF_3$, beta $AlF_3$, delta $AlF_3$, eta $AlF_3$, gamma $AlF_3$, kappa $AlF_3$ and/or theta $AlF_3$). Of note are aluminum fluorides, which are primarily alpha $AlF_3$ and/or beta $AlF_3$.

By fluorided alumina is meant a composition comprising aluminum, oxygen and fluorine. The fluoride content of the fluorided alumina can vary over a wide range, from about 0.001% to about 67.8% by weight. Of note are fluorided aluminas containing from 0.001% to about 10% by weight fluorine. The remainder of the fluorided alumina component will include aluminum and oxygen. The composition may also contain a minor amount (compared to aluminum) of silicon, titanium, phosphorus, zirconium and/or magnesium. The support material comprising fluorided aluminas and/or an aluminum fluoride may be prepared by a variety of methods. For example, U.S. Pat. Nos. 4,275,046, 4,902,838 and 5,243,106 disclose the preparation of fluorided alumina by the reaction of alumina with a vaporizable fluorine-containing fluorinating compound. Suitable fluorinating compounds include HF, $CCl_3F$, $CCl_2F_2$, $CHClF_2$, $CH_3CHF_2$, $CCl_2FCClF_2$ and $CHF_3$. U.S. Pat. No. 5,243,106 discloses the preparation of a high purity $AlF_3$ from aluminum sec-butoxide and HF.

Metals can be supported on aluminum fluoride or on fluorided alumina in a variety of ways. For example, U.S. Pat. No. 4,766,260 discloses the preparation of metals such as cobalt on a fluorided alumina support using impregnation techniques to support the metal. U.S. Pat. No. 5,559,069 discloses the preparation of a multiphase catalyst composition comprising various metal fluorides including cobalt fluoride homogeneously dispersed with aluminum fluoride. PCT International Publication No. 97/19751 discloses the preparation of multiphase catalyst compositions comprising metallic ruthenium homogeneously dispersed with various metal fluorides including aluminum fluoride.

Phases of aluminum fluoride such eta, beta, theta and kappa can be prepared as described in U.S. Pat. No. 5,393,509, U.S. Pat. No. 5,417,954 and U.S. Pat. No. 5,460,795.

Preparation

The catalysts of the present invention may be prepared by methods known to those skilled in the art. These include impregnating the catalytically active compounds or precursors onto a support, extruding one or more catalytically active compounds or precursors together with support material to prepare catalyst extrudates and/or precipitating the catalytically active compounds or precursors onto a support. The most preferred method of preparation may vary, depending for example on the desired catalyst particle size. Those skilled in the art are able to select the most suitable method for a given set of requirements.

One method of preparing a supported metal catalyst (e.g., a supported cobalt catalyst) is by incipient wetness impregnation of the support with an aqueous solution of a soluble metal salt such as nitrate, acetate, acetylacetonate or the like. Another method involves preparing the catalyst from a molten metal salt. For example, the support can be impregnated with a molten metal nitrate (e.g., $Co(NO_3)_2 \cdot 6H_2O$). Alternatively, the support can be impregnated with a solution of zero-valent cobalt such as $Co_2(CO)_8$, $Co_4(CO)_{12}$, or the like, in a suitable organic solvent (e.g., toluene). The impregnated support is dried and reduced with hydrogen. The hydrogen reduction step may not be necessary if the catalyst is prepared with zero valent cobalt. In another embodiment, the impregnated support is dried, oxidized with air or oxygen and reduced with hydrogen.

Typically, at least part of the metal component(s) of the catalysts of the present invention are present in a reduced state, i.e., metallic state. Therefore, it is normally advantageous to activate the catalyst prior to use by a reduction treatment, in the presence of hydrogen at an elevated temperature. This is typically accomplished by treating the catalyst with hydrogen at a temperature in the range of from about 75 to about 500° C., for about 0.5 to about 16 hours at a pressure of about 1 to about 75 atm. Pure hydrogen may be used in the reduction treatment as well as a mixture of hydrogen and an inert gas such as nitrogen. The amount of hydrogen may range from about 1% to about 100% by volume.

Feed Gas

The feed gases charged to the invention process must comprise hydrogen or a hydrogen source and carbon monoxide. $H_2/CO$ mixtures suitable as a feedstock for conversion to hydrocarbons according to the process of this invention can be obtained from light hydrocarbons such as methane by means of steam reforming or partial oxidation or can alternatively be provided by the gasification of coal. The hydrogen is preferably provided by free hydrogen, although some Fischer-Tropsch catalysts have sufficient water gas shift activity to convert some water to hydrogen for use in the Fischer-Tropsch process. It is preferred that the mole ratio of hydrogen to carbon monoxide in the feed is greater than 1:1. A preferred feed gas stream contains hydrogen and carbon monoxide in a molar ratio of about 2:1. A preferred range of hydrogen to carbon monoxide mole ratios is from 1.0 to 2.5. The feed gas may also contain carbon dioxide. The feed gas stream should contain a low concentration of compounds or elements that have a deleterious effect on the catalyst. Hence, the feed gas may need to be treated to ensure low concentrations of sulfur or nitrogen compounds such as hydrogen sulfide, ammonia and carbonyl sulfides.

Reaction Zone

The feed gas is contacted with the catalyst in a reaction zone. Mechanical arrangements of conventional design may be employed as the reaction zone. For example, fixed bed, slurry phase, slurry bubble column or ebulliating bed reactors. Accordingly, the size of the catalyst particles may vary depending on the reactor in which they are to be used.

The process of the invention may be performed in a fluid bed or a fixed bed or in a slurry in a liquid e.g. liquid hydrocarbon product. The activation of the catalyst may be performed in the same or a different reactor.

The gas hourly space velocity through the reaction zone may range from about 100 v/hr/v to about 5000 v/hr/v, preferably from about 300 v/hr/v to about 1500 v/hr/v. The reaction zone temperature is in the range from about 160° C. to about 300° C. Preferably, the reaction zone is operated at conversion promoting conditions at temperatures from about 190° C. to about 260° C. The reaction zone pressure is in the range of about 80 psig (653 kPa) to about 1000 psig (6994 kPa), preferably, from 80 psig (653 kPa) to about 600 psig (4237 kPa), more preferably, from about 140 psig (1066 kPa) to about 400 psig (2858 kPa).

The process products will have a great range of molecular weights. Typically, the carbon number range of the product hydrocarbons will start at methane and continue to the limits observable by modem analysis, about 50 to 100 carbons per molecule. Preferably, the product hydrocarbons are primarily paraffins.

The wide range of hydrocarbon species produced in the reaction zone will typically afford liquid phase products at the reaction zone operating conditions. Therefore the effluent stream of the reaction zone will often be a mixed phase stream. The effluent stream of the reaction zone may be cooled to effect the condensation of additional amounts of hydrocarbons and passed into a vapor-liquid separation zone. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column wherein they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

The following Examples contain descriptions and results for both continuous and batch tests of catalysts in accordance with the present invention.

General Procedure for Continuous Tests

The continuous testing unit comprised a syngas feed system, a tubular reactor, which had a set of wax and cold traps, back pressure regulators, and three gas chromatographs (one on-line and two off-line).

The carbon monoxide was purified before being fed to the reactor over a 22% lead oxide on alumina catalyst placed in a trap to remove any iron carbonyls present. The individual gases or mixtures of the gases were mixed in a 300 mL vessel filled with glass beads before entering the supply manifold feeding the reactor.

The reactor was made of ⅜ in. (0.95 cm) O.D. by ¼ in. (0.63 cm) I.D. stainless steel tubing. The length of the reactor tubing was 14 in. (35.6 cm). The actual length of the catalyst bed was 10 in. (25.4 cm) with 2 in. (5.1 cm) of 25/30 mesh (0.71/0.59 mm) glass beads and glass wool at the inlet and outlet of the reactor.

The wax and cold traps were made of 75 mL pressure cylinders. The wax traps were set at 140° C. while the cold traps were set at 0C. The reactor had two wax traps in parallel followed by two cold traps in parallel. At any given time products from the reactor flowed through one wax and one cold trap in series. Following a material balance period, the hot and cold traps used were switched to the other set in parallel, if needed. The wax traps collected a heavy hydrocarbon product distribution (usually between $C_6$ and above) while the cold traps collected a lighter hydrocarbon product distribution (usually between $C_3$ and $C_{20}$). Water, a major product of the Fischer-Tropsch process was collected in both the traps.

General Analytical Procedure

The uncondensed gaseous products from the reactors were analyzed using a common on-line HP Refinery Gas Analyzer. The Refinery Gas Analyzer was equipped with two thermal conductivity detectors and measured the concentrations of CO, $H_2$, $N_2$, $CO_2$, $CH_4$, $C_2$ to $C_5$ alkenes/alkanes/isomers and water in the uncondensed reactor products.

The products from each of the hot and cold traps were separated into an aqueous and an organic phase. The organic phase from the hot trap was usually solid at room temperature. A portion of this solid product was dissolved in carbon disulfide before analysis. The organic phase from the cold trap was usually liquid at room temperature and was analyzed as obtained. The aqueous phase from the two traps was combined and analyzed for alcohols and other oxygenates.

Two off-line gas chromatographs equipped with flame ionization detectors were used for the analysis of the organic and aqueous phases collected from the wax and cold traps.

Catalyst Testing Procedure

Catalyst (3 g) to be tested was mixed with 4 grams of 25/30 mesh (0.71/0.59 mm) and 4 grams of 2 mm glass beads. The 14 in. (35.6 cm) tubular reactor was first loaded with 25/30 mesh (0.71/0.59 mm) glass beads so as to occupy 2 in. (5.1 cm) length of the reactor. The catalyst/glass bead mixture was then loaded and occupied 10 in. (25.4 cm) of the reactor length. The remaining 2 in. (5.1 cm) of reactor length was once again filled with 25/30 mesh (0.71/0.59 mm) glass beads. Both ends of the reactor were plugged with glass wool.

Catalyst activation was subsequently carried out using the following procedure. The reactor was heated to 120° C. under nitrogen flow (100 cc/min and 40 psig (377 kPa)) at a rate of 1.5° C./min. The reactor was maintained at 120° C. under these conditions for two hours for drying of the catalyst. At the end of the drying period, the flow was switched from nitrogen to hydrogen. The reactor was heated under hydrogen flow (100 cc/min and 40 psig (377 kPa)) at a rate of 1.4° C./min. to 350° C. The reactor was maintained at 350° C. under these conditions for sixteen hours for catalyst reduction. At the end of the reduction period, the flow was switched back to nitrogen and the reactor cooled to reaction temperature (usually 220° C.).

The reactor was pressurized to the desired reaction pressure and cooled to the desired reaction temperature. Syngas, with a 2:1 $H_2$/CO ratio was then fed to the reactor when reaction conditions were reached.

The first material balance period started at about four hours after the start of the reaction. A material balance period lasted for between 16 to 24 hours. During the material balance period, data was collected for feed syngas and exit uncondensed gas flow rates and compositions, weights and compositions of aqueous and organic phases collected in the wax and cold traps, and reaction conditions such as temperature and pressure. The information collected was then analyzed to get a total as well as individual carbon, hydrogen and oxygen material balances. From this information, CO Conversion (%), Selectivity/Alpha plot (based on the Anderson Schulz Flory distribution) for all ($C_1$ to $C_{40}$) of the hydrocarbon products, $C_{5+}$ productivity (g/hr/kg cat), weight percent $CH_4$ in hydrocarbon products (%) and other desired reactor outputs were calculated.

The results obtained from the continuous-flow Fischer-Tropsch catalyst testing unit are shown in Table 1. This table lists the catalyst composition, CO Conversion (%), Alpha value from the Anderson-Shultz-Flory plot of the hydrocarbon product distribution, weight percent methane in the total hydrocarbon product (%), $C_{5+}$ productivity (g $C_{5+}$/hour/kg catalyst), $C_5$ olefin:paraffin ratio and $CC_{15}$ olefin:paraffin ratio. The temperature was 220° C., the pressure was 350 psig (2514 kPa) and the space velocity was 2 NL/hour/g. cat. for all the examples in Table 1.

Continuous Test Catalyst Preparation

Comparative Example A $Al_2O_3$ (120 g) was treated in a rotary evaporator at 70° C. with an aqueous solution containing $Co(NO_3)_2.6H_2O$ (59.2 g). The material was calcined at 250° C. under 1500 mL/min of air to obtain a catalyst with a nominal composition of 10% $Co/Al_2O_3$. Measurements of this catalyst were made after 51 and 140 hours of running.

Comparative Example B

10% $Co/Al_2O_3$ (86.9 g) material was treated at room temperature in a rotary evaporator with an acetone solution of Ru(acetylacetonate)$_3$ (0.345 g). The slurry was evaporated to dryness to obtain a catalyst with a nominal composition of 10% Co/0.1% $Ru/Al_2O_3$.

Example 1

10% Co/0.1% $Ru/Al_2O_3$ (20 g) was slurried in an aqueous solution of $AgNO_3$ (0.315 g) at 70° C. in a rotary evaporator and evaporated to dryness. The material was calcined at 250° C. under 1500 mL/min of air to obtain a catalyst with a nominal composition of 10% Co/0.1% Ru/1% $Ag/Al_2O_3$.

Example 2

10% Co/0.1% $Ru/Al_2O_3$ (20 g) was slurried in an aqueous solution of $AgNO_3$ (0.79 g) at 70° C. in a rotary evaporator and evaporated to dryness. The material was calcined at 250° C. under 1500 mL/min of air to obtain a catalyst with a nominal composition of 10% Co/0.1% Ru/2.51% $Ag/Al_2O_3$. Measurements of this catalyst were made after 46 and 70 hours of running.

Example 3

10% Co/0.1% $Ru/Al_2O_3$ (20 g) was slurried in an aqueous solution of $AgNO_3$ (3.15 g) at 70° C. in a rotary evaporator and evaporated to dryness. The material was calcined at 250° C. under 1500 mL/min of air to obtain a catalyst with a nominal composition of 10% Co/0.1% Ru/10% $Ag/Al_2O_3$.

Measurements of this catalyst were made after 39 and 138 hours of running.

TABLE 1

| Ex. No. | Catalyst | Cat. Age (h) | % CO Conv. | % Mass Balance | $C_{5+}$ | $C_5$ (o/p) | $C_{15}$ (o/p) |
|---|---|---|---|---|---|---|---|
| A | 10% Co/Al$_2$O$_3$ | 51 | 35.1 | 102 | 103 | 0.989 | 0.0475 |
|   |   | 140 | 31.6 | — | 95 | — | — |
| B | 10% Co/0.1% Ru/Al$_2$O$_3$ | 39 | 43.6 | 98 | 121 | 0.857 | 0.0302 |
| 1 | 10% Co/0.1% Ru/1% Ag/Al$_2$O$_3$ | 43 | 42.5 | 108 | 124 | 0.624 | 0.178 |
| 2 | 10% Co/0.1% Ru/2.5% Ag/Al$_2$O$_3$ | 46 | 60.4 | 101 | 128 | 0.608 | 0.087 |
| 3 | 10% Co/0.1% Ru/10% Ag/Al$_2$O$_3$ | 39 | 48.1 | 101 | 137 | 0.623 | 0.0196 |
|   |   | 138 | 67 | — | 164 | — | — |

General Procedure For Batch Tests

Each of the catalyst samples was treated with hydrogen prior to use in the Fischer-Tropsch reaction. The catalyst sample was placed in a small quartz crucible in a chamber and purged with 500 sccm (8.3×10$^{-6}$ m$^3$/s) nitrogen at room temperature for 15 minutes. The sample was then heated under 100 sccm (1.7×10$^{-6}$ m$^3$/s) hydrogen at 1° C./minute to 100° C. and held at 100° C. for one hour. The catalysts were then heated at 1° C./minute to 400° C. and held at 400° C. for four hours under 100 sccm (1.7×10$^{-6}$ m$^3$/s) hydrogen. The samples were cooled in hydrogen and purged with nitrogen before use.

A 2 mL pressure vessel was heated at either 200° C. or 225° C. under 1000 psig (6994 kPa) of H$_2$:CO (2:1) and maintained at that temperature and pressure for 1 hour when heated at 225° C. or for 6 hours when heated at 200° C. In a typical run, roughly 50 mg of the hydrogen catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of C$_{11}$-C$_{40}$ were analyzed relative to the internal standard. The lower hydrocarbons were not analyzed, since they are masked by the solvent and are also vented as the pressure is reduced.

A C$_{11+}$ productivity (g C$_{11+}$/hour/kg catalyst) was calculated based on the integrated production of the C$_{11}$-C$_{40}$ hydrocarbons per kg of catalyst per hour. The logarithm of the weight fraction for each carbon number ln(W$_n$/n) was plotted as the ordinate vs. number of carbon atoms in (W$_n$/n) as the abscissa. From the slope, a value of alpha was obtained. Some runs displayed a double alpha as shown in the tables. The results of runs over a variety of catalysts at 225° C. are shown in Table 2.

Batch Test Catalyst Preparation

Comparative Example C

Gamma-alumina (8 g) was treated in a rotary evaporator at 70° C. with an aqueous solution containing AgNO$_3$ (1.24 g). The material was calcined at 250° C. in 1.5 L/min of air to obtain a catalyst with a nominal composition of 10% Ag/Al$_2$O$_3$.

Example 4

A sample of eta-Al$_2$O$_3$ was crushed and sieved to 14/25 mesh (1.4/0.71 mm). Part of this material (30 g) was treated in a rotary evaporator at 70° C. with an aqueous solution containing Co(NO$_3$)•6H$_2$O (22.2 g). The Co-doped alumina was then calcined at 250° C. in 1.5 L/min air. Part of the calcined material (15.1 g) was treated in a rotary evaporator at 70° C. with an aqueous solution containing Co(NO$_3$)•6H$_2$O (3.5 g) and Pt(NH$_3$)$_4$(NO$_3$)$_2$ (5 mg). A portion of this Co-Pt-doped alumina (8 g) was treated in a rotary evaporator at 70° C. with an aqueous solution containing AgNO$_3$ (0.32 g). It was calcined at 250C. in 1.5l/min air.

Example 5

WO$_3$-doped ZrO$_2$ (50 g) was treated in a rotary evaporator at 70° C. with an aqueous solution containing Co(NO$_3$)•6H$_2$O (40 g) followed by calcination at 250° C. in 1.5 L/min air. A portion of the calcined material (20 g) was treated in a rotary evaporator at 70° C. with an aqueous solution containing AgNO$_3$ (0.62 g), then calcined at 250° C. in 1.5 L/min air. A portion of this calcined material (2 g) was treated in a rotary evaporator at 70° C. with an aqueous solution containing Co(NO$_3$)•6H$_2$O (1.4 g). The material was calcined at 250° C. in 1.5 L/min of air to obtain a catalyst with a nominal composition of 25% Co/2% Ag/WO$_3$—ZrO$_2$.

Example 6

A commercial sample (5 g) of Chimet 20% Co/Al$_2$O$_3$ was treated in a rotary evaporator at 70° C. with an aqueous solution containing AgNO$_3$ (0.155 g). The material was calcined at 250° C. in 1.5 L/min of air to obtain a catalyst with a nominal composition of 20% Co/2% Ag/Al$_2$O$_3$.

Example 7

MCM-41 (10.5 g), prepared according to J. S. Beck et al., JACS vol. 114, 1992, pp. 10834-10843, was treated in a rotary evaporator at 70° C. with an aqueous solution containing Co(NO$_3$)•6H$_2$O (8.4 g) followed by calcination at 250° C. in 1.5 L/min air. A portion of this material (3.7 g) was treated in a rotary evaporator at 70° C. with an aqueous solution containing Co(NO$_3$)•6H$_2$O (2.6 g) and AgNO$_3$ (0.115 g). The doped MCM-41 was calcined at 250° C. in 1.5 L/min of air to obtain a catalyst with a nominal composition of 25% Co/2% Ag/MCM-41.

Example 8

H-beta zeolite (12.5 g) was treated in a rotary evaporator at 70° C. with an aqueous solution containing Co(NO$_3$)•6H$_2$O (10 g) followed by calcination at 250° C. in 1.5 L/min air. A sample of this cobalt-doped zeolite (2 g) was treated in a rotary evaporator at 70° C. with an aqueous solution containing Co(NO$_3$)•6H$_2$O (1.4 g) and AgNO$_3$ (62 mg). The doped H-beta zeolite was calcined at 250° C. in 1.5 L/min of air to obtain a catalyst with a nominal composition of 25% Co/2% Ag/H-Beta.

Example 9

Al$_2$O$_3$ (Chimet, 10 g) was treated in a rotary evaporator at 70° C. with an aqueous solution containing Co(NO$_3$)

•6H$_2$O (10 g) followed by calcination at 250° C. in 1.5 L/min air. A sample of this cobalt-doped alumina (5.8 g) was treated in a rotary evaporator at 70° C. with an aqueous solution containing Co(NO$_3$)•6H$_2$O (4.06 g) and RuCl$_3$ (11 mg) followed by calcination at was calcined at 250° C. in 1.5 L/min of air. A sample of this calcined material (1 g) was treated in a rotary evaporator at 70° C. with an aqueous solution containing AgNO$_3$ (31 mg). The doped alumina was calcined at 250° C. in 1.5 L/min of air to obtain a catalyst with a nominal composition of 25% Co/0.1% Ru/2% Ag/Al$_2$O$_3$.

Example 10

WO$_3$-doped ZrO$_2$ (50 g) was treated in a rotary evaporator at 70° C. with an aqueous solution containing Co(NO$_3$)$_2$•6H$_2$O (40 g) followed by calcination at 250° C. in 1.5 L/min air. A portion of this material (20 g) was treated in a rotary evaporator at 70° C. with an aqueous solution containing Co(NO$_3$)$_2$•6H$_2$O (14 g) and AgNO$_3$ (0.62 g) followed by calcination at 250° C. in 1.5 L/min air. A sample of this material (1 g) was treated in a rotary evaporator at room temperature with an acetone solution of Ru(acac)$_3$ and dried to obtain a catalyst with a nominal composition of 25% Co/2% Ag/0.1% Ru/WO$_3$—ZrO$_2$.

Example 11

Sylopol™ SiO$_2$ (7 g) was treated in a rotary evaporator at 70° C. with an aqueous solution containing Co(NO$_3$)•6H$_2$O (7.4 g) and RuCl$_3$ (14 mg) followed by calcination at 250° C. in 1.5 L/min air. A sample of this material (1 g) was treated in a rotary evaporator at 70° C., with an aqueous solution containing AgNO$_3$ (31 mg) to obtain a catalyst with a nominal composition of 20% Co/0.1% Ru/2% Ag/Sylopol SiO$_2$.

Example 12

Anhydrous AlF$_3$ (50 g) was treated in a rotary evaporator at 70° C. with an aqueous solution containing Co(NO$_3$)•6H$_2$O (40 g) followed by two calcinations at 250° C. in 1.5 L/min air. A sample of this material (50 g) was treated in a rotary evaporator at 70° C. with an aqueous solution containing Co(NO$_3$)•6H$_2$O (35 g) and Pt(NH$_3$)$_4$(NO$_3$)$_2$ (50 mg) followed by calcination at 250° C. in 1.5 L/min air. A portion of this material (15 g) was treated in a rotary evaporator at 70° C. with an aqueous solution containing AgNO$_3$ (1.18 g) followed by calcination at 250° C. in 1.5 L/min air to obtain a catalyst with a nominal composition of 25% Co/0.05% Pt/5% Ag/AlF$_3$.

Example 13

Fluorided Al$_2$O$_3$ (45.2 g, Engelhard AI-4352), crushed and sieved to 14/25 mesh (1.4/0.71 mm) was treated in a rotary evaporator at 70° C. with an aqueous solution containing Co(NO$_3$)•6H$_2$O (26.6 g) and Pt(NH$_3$)$_4$(NO$_3$)$_2$ (38 mg) followed by calcination at 250° C. in 1.5 L/min air. A portion of this material (10 g) was treated in a rotary evaporator at 70° C. with an aqueous solution containing Co(NO$_3$)$_2$•6H$_2$O (7 g) and AgNO$_3$ (0.40 g) followed by calcination at 250° C. in 1.5 L/min air to obtain a catalyst with a nominal composition of 25% Co/0.05% Pt/3.5% Ag/Fluorided Al$_2$O$_3$.

Example 14

Bentonite (18 g, Engelhard, 956A-5-1841-17) was treated in a rotary evaporator at 70° C. with an aqueous solution containing Co(NO$_3$)•6H$_2$O (14.4 g) followed by calcination at 250° C. in 1.5 L/min air. The material was then treated in a rotary evaporator at 70° C. with an aqueous solution containing Co(NO$_3$)•6H$_2$O (12.6 g) and Pt(NH$_3$)$_4$(NO$_3$)$_2$ (18 mg) followed by calcination at 250° C. in 1.5 L/min air. A portion of this material (10 g) was treated in a rotary evaporator at 70° C. with an aqueous solution containing AgNO$_3$ (0.40 g) followed by calcination at 250° C. in 1.5 L/min air to obtain a catalyst with a nominal composition of 25% Co/0.5% Pt/2% Ag/Bentonite.

Example 15

Gamma Al$_2$O$_3$ (50 g, 140/230 mesh (0.11/0.062 mm)) was treated in a rotary evaporator at 70° C. with an aqueous solution containing Co(NO$_3$)•6H$_2$O (40 g) and AgNO$_3$ (7.5 g) followed by calcination at 250° C. in 1.5 L/min air. This material was then treated in a rotary evaporator at 70° C. with an aqueous solution containing Co(NO$_3$)•6H$_2$O (19 g) and Pt(NH$_3$)$_4$(NO$_3$)$_2$ (25 mg) followed by calcination at 250° C. in 1.5 L/min air to obtain a catalyst with a nominal composition of 20% Co/0.02% Pt/10% Ag/Al$_2$O$_3$.

Example 16

Trimethylphosphite-treated zeolite Rho (5.1 g) was treated in a rotary evaporator at 70° C. with an aqueous solution containing Co(NO$_3$)•6H$_2$O (4.1 g) followed by calcination at 250° C. in 1.5 L/min air. A portion of this material (2 g) was then treated in a rotary evaporator at 70° C. with an aqueous solution containing Co(NO$_3$)$_2$•6H$_2$O (14 g) and AgNO$_3$ (62 mg) followed by calcination at 250° C. in 1.5 L/min air to obtain a catalyst with a nominal composition of 25% Co/0.05% Pt/2% Ag/Zeolite RHO.

Example 17

TiO$_2$ (25.1 g) was treated in a rotary evaporator at 70° C. with an aqueous solution containing Co(NO$_3$)•6H$_2$O (20.1 g) followed by calcination at 250° C. in 1.5 L/min air. This material was then treated in a rotary evaporator at 70° C. with an aqueous solution containing Co(NO$_3$)•6H$_2$O (17.6 g) and Pt(NH$_3$)$_4$(NO$_3$)$_2$ (25 mg) followed by calcination at 250° C. in 1.5 L/min air. A portion of this material (5 g) was treated in a rotary evaporator at 70° C. with an aqueous solution containing AgNO$_3$ (0.155 g) followed by calcination at 250° C. in 1.5 L/min air to obtain a catalyst with a nominal composition of 25% Co/0.05% Pt/25% Ag/TiO$_2$.

Example 18

WO$_3$-doped ZrO$_2$ (50 g, Engelhard) was treated in a rotary evaporator at 70° C. with an aqueous solution containing Co(NO$_3$)•6H$_2$O (40 g) followed by calcination at 250° C. in 1.5 L/min air. Part of this material (25 g) of 92245-135-1 was treated in a rotary evaporator at 70° C. with an aqueous solution containing Co(NO$_3$)•6H$_2$O (17.5 g) and Pt(NH$_3$)$_4$(NO$_3$)$_2$ (25 mg) followed by calcination at 250° C. in 1.5 L/min air. Part of this material (4 g) was treated in a rotary evaporator at 70° C. with an aqueous solution containing AgNO$_3$ (0.124 g) followed by calcination at 250° C. in 1.5 L/min air to obtain a catalyst with a nominal composition of 25% Co/0.05% Pt/2% Ag/WO$_3$—ZrO$_2$.

Example 19

Gamma-Al$_2$O$_3$ (20 g) was treated in a rotary evaporator at 70° C. with an aqueous solution containing Co(NO$_3$)•6H$_2$O (16 g) followed by calcination at 250° C. in 1.5 L/min air.

This material was then treated in a rotary evaporator at 70° C. with an aqueous solution containing $Co(NO_3)\cdot 6H_2O$ (14 g) and $Pt(NH_3)_4(NO_3)_2$ (20 mg) followed by calcination at 250° C. in 1.5 L/min air. Part of this material (1 g) was treated in a rotary evaporator at 70° C. with an aqueous solution containing $AgNO_3$ (31 mg) followed by calcination at 250° C. in 1.5 L/min air to obtain a catalyst with a nominal composition of 25% Co/0.05% Pt/2% Ag/$Al_2O_3$.

Example 20

Sylopol™ $SiO_2$ (25 g) was calcined at 1° C./min to 200° C., where it was kept for 4 hours. Part of this material (8 g) was treated in a rotary evaporator at 70° C. with an aqueous solution containing $Co(NO_3)\cdot 6H_2O$ (6.4 g) followed by calcination at 250° C. in 1.5 L/min air. This material was then treated in a rotary evaporator at 70° C. with an aqueous solution containing $Co(NO_3)\cdot 6H_2O$ (5.6 g) and $Pt(NH_3)_4(NO_3)_2$ (8 mg) followed by calcination at 250° C. in 1.5 L/min air. Part of this material (2 g) was treated in a rotary evaporator at 70° C. with an aqueous solution containing $AgNO_3$ (62 mg) followed by calcination at 250° C. in 1.5 L/min air to obtain a catalyst with a nominal composition of 25% Co/0.05% Pt/2% Ag/Sylopol™ $SiO_2$.

Example 21

$SiO_2/Al_2O_3$ (20 g, 14/25mesh (1.4/0.71 mm)) was treated in a rotary evaporator at 70° C. with an aqueous solution containing $Co(NO_3)\cdot 6H_2O$ (16 g) followed by calcination at 250° C. in 1.5 L/min air. A portion of this material (7 g) was treated in a rotary evaporator at 70° C. with an aqueous solution containing $Co(NO_3)\cdot 6H_2O$ (4.9 g) and $Pt(NH_3)_4(NO_3)_2$ (7 mg) followed by calcination at 250° C. in 1.5 L/min air. A portion of this material was then (2 g) treated in a rotary evaporator at 70° C. with an aqueous solution containing $AgNO_3$ (62 mg) followed by calcination at 250° C. in 1.5 L/min air to obtain a catalyst with a nominal composition of 25% Co/0.05% Pt/2% Ag/$SiO_2$—$Al_2O_3$.

Example 22

High pore volume $Al_2O_3$ (20 g, Engelhard 6568-2-1) was treated in rotary evaporator at 70° C. with an aqueous solution containing $Co(NO_3)\cdot 6H_2O$ (16 g) followed by calcination at 250° C. in 1.5 L/min air. A portion of this material (5 g) was treated in a rotary evaporator at 70° C. with an aqueous solution containing $Co(NO_3)\cdot 6H_2O$ (3.5 g) and $Re_2O_7$ (65 mg) followed by calcination at 250° C. in 1.5 L/min air. A portion of this material (1 g) was then (2 g) treated in a rotary evaporator at 70° C. with an aqueous solution containing $AgNO_3$ (31 mg) followed by calcination at 250° C. in 1.5 L/min air to obtain a catalyst with a nominal composition of 25% Co/1% Re/2% Ag/$Al_2O_3$.

TABLE 2

(225° C.)

| Ex. No. | Co | Pt | Ag | Other | Support | $C_{11+}$ Productivity | Alpha |
|---|---|---|---|---|---|---|---|
| C |  |  | 10 |  | $Al_2O_3$ | <1 | N.D. |
| 4 | 15 |  | 2.5 |  | Sulfated $ZrO_2$ | 108 | 0.86 |
| 5 | 25 |  | 2 |  | $WO_3$—$ZrO_2$ | 59 | 0.88 |
| 6 | 20 |  | 2 |  | $Al_2O_3$ | 315 | 0.88 |
| 7 | 25 |  | 2 |  | MCM-41 | 240 | 0.91 |
| 8 | 25 |  | 2 |  | H-Beta | 91 | 0.89 |

TABLE 2-continued (225° C.)

| Ex. No. | Co | Pt | Ag | Other | Support | $C_{11+}$ Productivity | Alpha |
|---|---|---|---|---|---|---|---|
| 9 | 25 |  | 2 | 0.1 Ru | $Al_2O_3$ | 388 | 0.9 |
| 10 | 25 |  | 2 | 0.1 Ru | $WO_3$—$ZrO_2$ | 70 | 0.8 |
| 11 | 20 |  | 2 | 0.1 Ru | Sylopol™ $SiO_2$ | 207 | 0.88 |
| 12 | 25 | 0.5 | 5 |  | $AlF_3$ | 44 | 0.82/0.93 |
| 13 | 25 | 0.5 | 3.5 |  | Fluorided $Al_2O_3$ | 128 | 0.86 |
| 14 | 25 | 0.5 | 2 |  | Bentonite | 77 | 0.84/0.93 |
| 15 | 20 | 0.02 | 10 |  | $Al_2O_3$ | 374 | 0.91 |
| 16 | 25 | 0.05 | 2 |  | Zeolite RHO | 73 | 0.84/0.68 |
| 17 | 25 | 0.05 | 25 |  | $TiO_2$ | 294 | 0.92 |
| 18 | 25 | 0.05 | 2 |  | $WO_3$—$ZrO_2$ | 70 | 0.89 |
| 19 | 25 | 0.05 | 2 |  | $Al_2O_3$ | 344 | 0.87 |
| 20 | 25 | 0.05 | 2 |  | Sylopol™ $SiO_2$ | 227 | 0.88 |
| 21 | 25 | 0.05 | 2 |  | $SiO_2$—$Al_2O_3$ | 88 | 0.86 |
| 22 | 25 |  | 2 | 1 Re | $Al_2O_3$ | 278 | 0.9 |
| 23 | 25 |  | 2 | 0.1 Pd | $Al2O3$ | 19.3 | 0.88 |

Further experiments were run in a similar fashion in order to obtain data comparing silver-containing catalysts to catalysts having a similar composition and support but lacking silver. The results of these experiments are set out in Table 3. Test results are grouped by support type. As can be seen, the addition of silver to a catalyst formulation generally increases the $C_{11+}$ productivity of that formulation, and raises its alpha to an acceptable level (i.e. >0.8).

TABLE 3

| | Catalyst Description | | | | | $C_{11+}$ Productivity | Alpha |
|---|---|---|---|---|---|---|---|
| | Co | Pt | Ag | Other | Support | | |
| Group 1 | | | | | | | |
| 24 | 20 |  |  |  | $Al_2O_3$ | 173 | 0.9 |
| 25 | 20 |  | 2 |  | $Al_2O_3$ | 203 | 0.88 |
| 26 | 20 | 0.041 |  |  | $Al_2O_3$ | 209 | 0.88 |
| 27 | 20 | .025 | 2 |  | $Al_2O_3$ | 225 | 0.94 |
| Group 2 | | | | | | | |
| 28 | 20 | 0.041 |  |  | $Al_2O_3$ | <1 | <1 |
| 29 | 8.9 | 0.032 | 0.9 |  | $Al_2O_3$ | 140 | 0.84/0.93 |
| 30 | 10 |  |  |  | $Al_2O_3$ | <1 | <1 |
| Group 3 | | | | | | | |
| 31 | 16 |  |  |  | $AlF_3$ | <1 | <1 |
| 32 | 30 | 0.05 |  |  | $AlF_3$ | <1 | <1 |
| 33 | 25 | 0.05 | 5 |  | $AlF_3$ | 44.2 | 0.82/0.93 |
| Group 4 | | | | | | | |
| 34 | 25 | 0.05 |  |  | Bentonite | <1 | <1 |
| 35 | 25 | 0.5 | 2 |  | Bentonite | 76.9 | 0.84/0.93 |
| Group 5 | | | | | | | |
| 36 | 25 | 0.05 |  |  | MCM-41 | 33.6 | 0.83 |
| 37 | 25 |  | 2 |  | MCM-41 | 48.5 | 0.83 |
| Group 6 | | | | | | | |
| 38 | 25 | 0.05 |  |  | Zeolite (TMP) (Calsicat) | 37.7 | 0.81/0.62 |
| 39 | 25 | 0.05 | 2 |  | Zeolite (TMP) (Calsicat) | 50 | 0.82/0.51 |

TABLE 3-continued

| Catalyst Description | | | | $C_{11+}$ Productivity | Alpha |
|---|---|---|---|---|---|
| Co | Pt | Ag | Other Support | | |
| Group 7 | | | | | |
| 40 | 25 | 0.05 | C-SiO2 | 119 | 0.87 |
| 41 | 25 | 0.05 | 2 C-SiO2 | 181 | 0.87 |

What is claimed is:

1. A process for producing hydrocarbons, comprising contacting a feed stream comprising hydrogen and carbon monoxide with a catalyst in a reaction zone maintained at conversion-promoting conditions effective to produce an effluent stream comprising hydrocarbons, said conversion-promoting conditions including temperatures not greater than about 225° C., wherein the catalyst comprises (a) cobalt, (b) catalyst support, and (c) silver, wherein the catalytic activity of the catalyst is increased by the addition of silver.

2. A process for producing hydrocarbons, comprising contacting a feed stream comprising hydrogen and carbon monoxide with a catalyst in a reaction zone maintained at conversion-promoting conditions effective to produce an effluent stream comprising hydrocarbons, said conversion-promoting conditions including temperatures not greater than about 225° C., wherein the catalyst comprises (a) cobalt, (b) catalyst support, (c) silver, and a promoter selected from the group consisting of rhenium, ruthenium, platinum and combinations thereof, wherein the catalytic activity of the catalyst is increased by the addition of silver.

3. The process of claim 1 wherein the ratio of cobalt to silver is between about 0.05 and about 2.

4. The process of claim 1 wherein the cobalt comprises from about 10 to about 30 mole percent of the total catalyst weight.

5. The process of claim 1 wherein the catalytically active metal comprises cobalt and platinum.

6. The process of claim 5 wherein the catalyst includes platinum, the cobalt content is from about 10 to about 25 mole percent, and the platinum content is from about 0.001 to 5 mole percent.

7. The process of claim 1 wherein the silver is present in an amount of from about 001% to about 10% based on the total weight of the catalyst.

8. The process of claim 1 wherein the produced hydrocarbons have a paraffin to olefin molar ratio for $C_{5+}$ hydrocarbons of at least 1.2:1.

9. The process of claim 1 wherein the support is selected from the group consisting of alumina, zirconia, silica, titania, and combinations thereof.

10. The process of claim 1 wherein the support is selected from the group consisting of $Al_2O_3$, $ZrO_2$, sulfated $ZrO_2$, $WO_3$—$ZrO_2$, MCM-41, H-Beta, Sylopol $SiO_2$, $AlF_3$, fluorided $Al_2O_3$, bentonite, Zeolite RHO, $TiO_2$, and $SiO_2$—$Al_2O_3$, molecular sieves, and combinations thereof.

11. The process of claim 1 wherein the catalyst comprises one or more promoters selected from the group consisting of Na, K, Rb, Cs, Mg, Ca, Sr, Ba, Cu, Ag, Au, Sc, Y, La, Ti, Zr, Hf, V, Nb, Ta, Rh, Pd, Os, Ir, Pt, Mn, B, P, and Re.

12. The process of claim 10 wherein the promoter comprises from about 0.001 to 20 mole percent of the total metal content.

13. A method for increasing the activity of a cobalt-containing Fischer-Tropsch catalyst for use in a Fischer-Tropsch reaction at temperatures not greater than 225° C., comprising adding an amount of silver to the catalyst.

* * * * *

UNITED STATES PATENT AND TRADEMARK OFFICE
CERTIFICATE OF CORRECTION

PATENT NO. : 6,602,921 B2 Page 1 of 1
DATED : August 5, 2003
INVENTOR(S) : Leo E. Manzer et al.

It is certified that error appears in the above-identified patent and that said Letters Patent is hereby corrected as shown below:

Column 16,
Line 11, "00.1%" should be -- 0.01% --.

Signed and Sealed this

Twenty-second Day of June, 2004

JON W. DUDAS
*Acting Director of the United States Patent and Trademark Office*